(12) United States Patent
Sohn

(10) Patent No.: US 9,808,438 B2
(45) Date of Patent: Nov. 7, 2017

(54) METHOD FOR TREATING MUCOSITIS

(71) Applicant: ENZYCHEM LIFESCIENCES CORPORATION, Seoul (KR)

(72) Inventor: Ki-Young Sohn, Seoul (KR)

(73) Assignee: Enzychem Lifesciences Corporation, Seoul (KR)

( * ) Notice: Subject to any disclaimer, the term of this patent is extended or adjusted under 35 U.S.C. 154(b) by 0 days.

(21) Appl. No.: 14/959,750

(22) Filed: Dec. 4, 2015

(65) Prior Publication Data

US 2017/0128404 A1 May 11, 2017

Related U.S. Application Data

(60) Provisional application No. 62/253,019, filed on Nov. 9, 2015.

(51) Int. Cl.

| *A61K 31/231* | (2006.01) |
| *A61K 9/00* | (2006.01) |
| *A61K 9/48* | (2006.01) |
| *A61K 45/06* | (2006.01) |
| *A61N 5/06* | (2006.01) |
| *A61N 5/067* | (2006.01) |

(52) U.S. Cl.
CPC .......... *A61K 31/231* (2013.01); *A61K 9/0053* (2013.01); *A61K 9/4825* (2013.01); *A61K 9/4858* (2013.01); *A61K 45/06* (2013.01); *A61N 5/0603* (2013.01); *A61N 2005/0606* (2013.01); *A61N 2005/067* (2013.01); *A61N 2005/0609* (2013.01)

(58) Field of Classification Search
None
See application file for complete search history.

(56) References Cited

U.S. PATENT DOCUMENTS

| 7,662,853 B2 | 2/2010 | Kim .............................. 514/547 |
| 2003/0166535 A1* | 9/2003 | Podolsky ............... A61K 38/22 514/2.4 |
| 2004/0029893 A1* | 2/2004 | Lane .................. A61K 31/4178 514/254.07 |
| 2008/0194877 A1* | 8/2008 | Letari ................... A61K 31/17 564/271 |
| 2008/0200543 A1 | 8/2008 | Kim .............................. 514/547 |
| 2009/0253923 A1 | 10/2009 | Lee et al. ........................ 554/79 |
| 2010/0035989 A1* | 2/2010 | Schwartz ............. A61K 31/232 514/560 |
| 2010/0137435 A1* | 6/2010 | Kim ....................... A61K 31/22 514/546 |
| 2010/0279959 A1* | 11/2010 | Gagnon ................. A61K 31/18 514/25 |
| 2014/0171438 A1* | 6/2014 | Pan .................. C07D 295/135 514/252.11 |
| 2016/0128966 A1 | 5/2016 | Han et al. ..................... 514/183 |
| 2016/0151323 A1 | 6/2016 | Han et al. ..................... 514/183 |
| 2016/0166528 A1 | 6/2016 | Kim et al. .................... 514/547 |

FOREIGN PATENT DOCUMENTS

| KR | 10-2000-0071887 | 11/2000 |
| KR | 10-2005-0103259 | 10/2005 |
| KR | 10-2006-0047447 | 5/2006 |
| KR | 10-2007-0010841 | 1/2007 |
| WO | WO 99/26640 | 6/1999 |
| WO | WO 2005/112912 | 12/2005 |
| WO | WO 2015/026114 | 2/2015 |

OTHER PUBLICATIONS

Letter/Writen Disclosure of the Supplemental Information Disclosure Statement for the above-referenced application, filed herewith Jun. 29, 2017, 2 pages.
Al-Tonbary et al., "Vitamin E and N-Acetylcysteine as Antioxidant Adjuvant Therapy in Children with Acute Lymphoblastic Leukemia," Advances in Hematology, vol. 2009, Article ID 689639, 5 pages (2009).
Cao et al., "Purification and structural identification of an autoinducer for the luminescence system of Vibrio harveyi," JBC 264:21670-21676 (1989).
Chang et al., "From hematopoietic stem cells to platelets," J. Thromb. and Haemost. 5(Suppl 1):318-327 (2007).
Gomez et al., "Blockade of Chemotherapy-Induced Thrombocytopenia by Bax Inhibiting Peptides (BIPs) in Mouse Model," Blood 110:281 (2007). Abstract, 2 pages.
Jones et al., "A randomised pilot Phase II study of doxorubicin and cyclophosphamide (AC) or epirubicin and cyclophosphamide (EC) given 2 weekly with pegfilgrastim (accelerated) vs 3 weekly (standard) for women with early breast cancer," Brit. J. Cancer 100:305-310 (2009).
Kavanagh, "An overview of immunomodulatory intervention in rheumatoid arthritis," Drugs Today 35(4-5):275-286 (1999). Abstract, 2 pages.
Kim et al., "Auranofin blocks interleukin-6 signalling by inhibiting phosphorylation of JAK1 and STAT3," Immunology 122(4): 607-614 (2007).
Kim et al., "EC-18, a synthetic monoacetyldiacylglyceride, inhbitis hematogenous metastasis of KIGB-5 biliary cancer cell in hamster model," Journal of Korean Medical Science 24:474-480 (2009).
Machine generated English language translation of Korean Publication No. KR 10-2005-0103259 published Oct. 27, 2005, accessed from Espacenet on Jun. 29, 2017, 15 pages.
Morstyn et al., "Treatment of chemotherapy-induced neutropenia by subcutaneously administered granulocyte colony-stimulating factor with optimization of dose and duration of therapy," J. Clin. Oncol. 7(10):1554-1562 (1989). Abstract, 2 pages.
Wambi et al., "Dietary Antioxidants Protect Hematopoietic Cells and Improve Animal Survival after Total-Body Irradiation," Radiat. Res. 169(4):384-396 (2008).

(Continued)

*Primary Examiner* — Robert A Wax
*Assistant Examiner* — Quanglong Truong
(74) *Attorney, Agent, or Firm* — Dentons US LLP; Stephanie Seidman

(57) ABSTRACT

The invention provides a pharmaceutical composition for preventing or treating mucositis, for example oral mucositis (e.g., oral ulceration) and gastrointestinal mucositis, comprising a monoacetyldiacylglycerol compound, especially PLAG, and a method of preventing or treating mucositis using the same.

27 Claims, No Drawings

(56) References Cited

OTHER PUBLICATIONS

Zuckerman, "Hematopoietic Abnormalities in Patients With Cancer," Cancer Control J. Suppl. 5(2 Suppl 1):1-4 (1998).
Office Action, dated Sep. 22, 2016, in connection with U.S. Appl. No. 14/936,464, 16 pages.
Response, submitted Jan. 23, 2017, to Office Action, dated Sep. 22, 2016, in connection with U.S. Appl. No. 14/936,464, 39 pages.
Final Office Action, dated Apr. 4, 2017, in connection with U.S. Appl. No. 14/936,464, 20 pages.
International Search Report and Written Opinion, dated Aug. 5, 2015, in connection with International Patent Application No. PCT/US2015/031204, 10 pages.
International Preliminary Report on Patentability, dated Nov. 15, 2016, in connection with International Patent Application No. PCT/US2015/031204, 8 pages.
Examination Report, dated Jun. 9, 2017, in connection with Australian Patent Application No. 2015258840, 5 pages.
Office Action, dated Sep. 22, 2016, in connection with U.S. Appl. No. 14/951,353, 16 pages.
Response, submitted Jan. 23, 2017, to Office Action, dated Sep. 22, 2016, in connection with U.S. Appl. No. 14/951,353, 41 pages.
Final Office Action, dated Apr. 4, 2017, in connection with U.S. Appl. No. 14/951,353, 15 pages.
Office Action, dated May 31, 2016, in connection with U.S. Appl. No. 15/048,732, 12 pages.
Response, filed Aug. 31, 2016, to Office Action, dated May 31, 2016, in connection with U.S. App. No. 15/048,732, 8 pages.
Final Office Action, dated Oct. 12, 2016, in connection with U.S. Appl. No. 15/048,732, 15 pages.
Request for Continued Examination and Amendment, filed Jan. 10, 2017, responsive to the Final Office action, dated Oct. 12, 2016, in connection with U.S. Appl. No. 15/048,732, 11 pages.
Supplemental Amendment and Response, filed Jan. 19, 2017, to Final Office Action, dated Oct. 12, 2016, n connection with U.S. Appl. No. 15/048,732, 8 pages.
Office Action, dated Feb. 14, 2017, in connection with U.S. Appl. No. 15/048,732, 15 pages.
International Search Report and Written Opinion, dated Dec. 17, 2014, in connection with International Patent Application No. PCT/KR2014/007631, 8 pages.
International Preliminary Report on Patentability, dated Feb. 23, 2016, in connection with International Patent Application No. PCT/KR2014/007631, 7 pages.
Examination Report, dated Sep. 5, 2016, in connection with Australian Patent Application No. 2014309637, 3 pages.
Response, filed Jan. 23, 2017, to Examination Report, dated Sep. 5, 2016, in connection with Australian Patent Application No. 2014309637, 19 pages.
Examination Report, dated Feb. 10, 2017, in connection with Australian Patent Application No. 2014309637, 3 pages.
Response, filed Apr. 21, 2017, to Examination Report, dated Feb. 10, 2017, in connection with Australian Patent Application No. 2014309637, 16 pages.
Notice of Acceptance, filed May 8, 2017, in connection with Australian Patent Application No. 2014309637, 3 pages.
Examination Search Report, dated May 4, 2017, in connection with Canadian Patent Application No. 2921845, 3 pages.
Extended European Search Report, dated Mar. 24, 2017, in connection with European Patent Application No. 14837360.8, 5 pages.

\* cited by examiner

METHOD FOR TREATING MUCOSITIS

CROSS-REFERENCE TO RELATED APPLICATIONS

This application claims priority from U.S. Provisional 62/253,019, filed 9 Nov. 2015, the content of which is incorporated herein by reference.

FIELD OF THE INVENTION

The invention relates to methods for preventing or treating mucositis, for example oral mucositis (e.g., oral ulceration) and gastrointestinal mucositis, comprising administration of a monoacetyldiacylglycerol compound, as well as compositions, more particularly, pharmaceutical compositions and health functional food compositions, useful therefor.

BACKGROUND OF THE INVENTION

Mucositis is a pathological condition characterized by mucosal damage, ranging from mild inflammation to deep ulcerations and affecting one or more parts of the alimentary tract from the mouth to the anus. Mucositis usually occurs as an adverse effect of treatment of diseases such as cancer. As a result of cell death in reaction to chemotherapy, the mucosal lining of the alimentary track such as the mouth becomes thin, may be inflamed and ulcerated. Radiotherapy to the head and neck or to the pelvis or abdomen can also cause oral or gastrointestinal mucositis. Oral and gastrointestinal (GI) mucositis affects many patients undergoing high-dose chemotherapy and hematopoietic stem cell transplantation (HSCT). Oral mucositis is particularly profound and prolonged among HSCT recipients who receive total-body irradiation.

Treatment-induced mucositis is one of the most debilitating and troublesome side effects from cancer therapy and affects quality of patient's life. The usual presentation of oral mucositis includes erythema and/or ulceration of the mucosa. In severe cases, the patient is unable to eat the solid food and even unable to consume liquids as well, resulting in the need for total parenteral nutrition (TPN). Gastrointestinal mucositis usually presents with pain, bloating, diarrhea, nausea and vomiting. As a result, mucositis is associated with considerable morbidity, diminished quality of life as well as negative health and economic outcomes. In addition, mucositis may interfere with the regular administration and dosing of programmed treatment plans, thus affecting the outcome of cancer treatment.

Oral ulceration is a very common presentation of oral mucositis, occurring in association with many diseases and by many different mechanisms. Recurrent oral ulceration is a condition in which a break or an erosion in the mucous membrane occurs recurrently in the mouth. The underlying cause of recurrent oral ulceration remains unclear. However, family tendency, trauma, hormonal factors, food or drug hypersensitivity, emotional stress, chemotherapy, irradiation therapy, neutropenic conditions and autoimmune diseases are known to be predisposing conditions for recurrent oral ulceration. For example, it is known that recurrent aphthous stomatitis (RAS), systemic lupus erthematosus (SLE) and Behcet's disease (BD) cause recurrent oral ulceration.

Recurrent aphthous stomatitis (RAS) is the most common cause of mouth ulcers. Aphthae are painful oral lesions that appear as localized, round shallow ulceration with a grayish base. The pathogenesis of aphthous ulcers is not well defined. Although the cause of aphthous stomatitis is not entirely clear, it is speculated that it is caused by bacteria infection, viral infection or immune dysregulation. It is also known that hot food, wound in the mouth, fatigue or allergy may cause aphthous stomatitis or exacerbate it.

Systemic lupus erythematosus (SLE) is a chronic systemic autoimmune disease, affecting many organs in the body such as skin, joint, kidney, lung and neuronal system. The exact cause of SLE is not known, but several factors such as genes, hormones and environment factors have been associated with SLE. Common symptoms of SLE include rash on cheeks and nose and mouth ulcers. SLE may also cause joint pain, kidney problems and depression.

Behcet's disease (BD) is a rare immune-mediated small-vessel systemic vasculitis that often presents with oral ulcers, genital ulcers and ocular problems. As a systemic disease, it can also affect many organs such as the gastrointestinal tract, pulmonary, musculoskeletal, cardiovascular and neurological systems. The most common symptoms include oral ulcers, genital ulcers, inflammation of the eye, skin lesions, and arthritis. The exact cause of SLE is not known, but several factors such as genetic factors and environment factors may be responsible for Behcet's disease.

To date, treatment of mucositis is mainly supportive. Oral hygiene is the mainstay of treatment. Currently, no approved preventive or therapeutic agent consistently prevents mucositis in all clinical settings. Palifermin, or human recombinant keratinocyte growth factor (KGF) significantly reduces the incidence, duration, and severity of oral mucositis in patients undergoing autologous HSCT and has been approved for use in patients with hematologic malignancies undergoing high-dose chemotherapy with or without concomitant total body irradiation, with autologous or allogeneic stem cell transplantation. Low-level laser therapy (LLLT) is another treatment that can reduce the severity of oral mucositis. It involves focusing low-energy lasers at affected tissue. LLLT is thought to work by stimulating certain cells that then help to speed up the healing process. In addition, two agents, Gelclair® and Zilactin®, are mucosal protectants that work by coating the mucosa, forming a protective barrier for exposed nerve endings. In clinical trials, these agents improved pain control and the ability to eat and speak Amifostine (Ethyol®), a drug that offers some protection against the damage to the mucosa caused by radiation, is approved by the FDA for patients receiving radiation therapy for cancers of the head and neck. Studies have demonstrated that Amifostine can reduce dry mouth and may prevent or lessen the degree of the mucositis. However, the measures to prevent or treat mucositis are inadequate and limited to the control of pain, infections, bleeding and nutrition. It would be desirable to have a new method for preventing or treating mucositis, especially in cancer patients.

Deer antler is a traditional Asian medicine that is widely used, prepared by drying uncornified antler of a deer (*Cornu cervi*). Deer antler has been acclaimed to have various medical effects such as growth- and development-promoting effects, promoting hematopoietic function, treating nervous breakdown, beneficial to cardiac insufficiency, improving the function of five viscera and six entrails, as described in the Dong-eui Bogam, a Korean medical book first published in 1613. In addition, deer antler has been known to have various medical effects such as boosting strength and endurance, improvement of myocardial motion, recovery from tiredness, enhancement of the immune system. Active ingredients of deer antler and their effects have been studied. For example, it has been reported that certain components of deer antler, including rac-1-palmitoyl-2-linoleoyl-3-acetyl-glycerol (PLAG) obtained from chloroform extracts of the deer antler, have growth-stimulating activities of hematopoietic stem cells and megakaryocytes (WO 99/26640). It has also been reported that monoacetyldiacylglycerol derivatives which are active components of the deer antlers are effective in treating autoimmune diseases, sepsis, cancers such as bile duct cancer, kidney cancer or malignant melanoma, and so on (WO 2005/112912).

BRIEF SUMMARY OF THE INVENTION

The inventors aimed to find a novel therapeutic for prevention and treatment of mucositis such as oral mucositis (e.g., oral ulceration) and gastrointestinal mucositis and surprisingly found that the monoacetyldiacylglycerols described herein, particularly PLAG, are effective in preventing or treating mucositis. Therefore, the present invention provides pharmaceutical compositions for preventing or treating mucositis and methods for preventing or treating mucositis by using the same.

In some embodiments, the present disclosure provides pharmaceutical compositions and health functional food compositions for preventing, improving or treating mucositis such as oral mucositis (e.g., oral ulceration) and gastrointestinal mucositis, comprising a monoacetyldiacylglycerol of Formula 1, particularly PLAG, as an active ingredient.

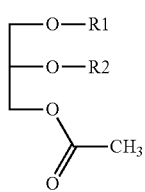

[Formula 1]

wherein $R_1$ and $R_2$ are independently a fatty acid residue of 14 to 20 carbon atoms.

In some embodiments, the present disclosure provides methods for preventing or treating mucositis such as oral mucositis (e.g., oral ulceration) and gastrointestinal mucositis, comprising administering an effective amount of a compound of formula 1, particularly PLAG, to a patient in need thereof.

Further areas of applicability of the present invention will become apparent from the detailed description and examples provided hereinafter. It should be understood that the detailed description and specific examples, while indicating certain preferred embodiments of the invention, are intended for purposes of illustration only and are not intended to limit the scope of the invention.

DETAILED DESCRIPTION OF THE INVENTION

Compositions of the present invention for preventing or treating mucositis such as oral mucositis (e.g., oral ulceration) and gastrointestinal mucositis comprise glycerol derivatives having one acetyl group and two acyl groups of the following Formula 1:

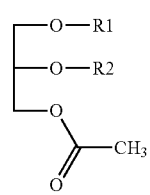

[Formula 1]

wherein $R_1$ and $R_2$ are independently a fatty acid residue of 14 to 20 carbon atoms.

In the present disclosure, the glycerol derivatives of Formula I are sometimes referred as monoacetyldiacylglycerols (MDAG). Fatty acid residue refers to the acyl moiety resulting from formation of an ester bond by reaction of a fatty acid and an alcohol. Non-limiting examples of $R_1$ and $R_2$ thus include palmitoyl, oleoyl, linoleoyl, linolenoyl, stearoyl, myristoyl, arachidonoyl, and so on. Preferable combinations of $R_1$ and $R_2$ ($R_1/R_2$) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyldiacylglycerol derivatives of Formula 1 can be (R)-form, (S)-form or a racemic mixture, and may include their stereoisomers. Where the $R_1$ and/or $R_2$ substituents are unsaturated fatty acid residues, the double bond(s) may have the cis configuration.

In one embodiment, the monoacetyldiacylglycerol is a compound of the following Formula 2:

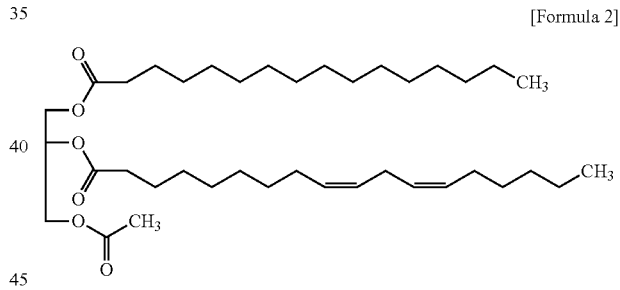

[Formula 2]

The compound of Formula 2 is 1-palmitoyl-2-linoleoyl-3-acetylglycerol, sometimes referred as "PLAG" in this disclosure. $R_1$ and $R_2$ of the compound of Formula 2 are palmitoyl and linoleoyl, respectively. The 2-carbon on the glycerol moiety is chiral. PLAG is generally provided as the racemate, and the R- and S-enantiomers appear to have the same activity. It is known that PLAG of Formula 2 increases survivability ratio of animals in sepsis animal model experiment using cecal-ligation-puncture, and shows no toxicity in a GLP (Good Laboratory Practice) toxicity test. However, the effect of the monoacetyldiacylglycerol compounds including PLAG on mucositis is not known or disclosed in the prior arts.

The monoacetyldiacylglycerol compounds can be separated and extracted from the natural deer antler or can be produced by conventional organic synthesis methods. More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacylglycerol compound for the present invention. A solvent for the extraction is selected among chloroform/methanol, hexane/ethylacetate/acetic acid, but not limited thereto. A chemical synthetic method for the preparation of monoacetyldiacylglycerol compounds is shown, for example, in Korean Registered Patents No. 10-0789323 and No. 10-1278874, the contents of which are incorporated herein by reference.

The monoacetyldiacylglycerol compound, especially PLAG, of the present invention is effective for preventing or treating mucositis such as oral mucositis (e.g., oral ulceration) and gastrointestinal mucositis. In vivo studies show that the administration of PLAG to the patients significantly improves the symptoms of oral ulceration.

In one embodiment, the present disclosure provides a method for preventing or treating mucositis, comprising administering an effective amount of a compound of formula 1, particularly PLAG, to a patient in need thereof. In the present disclosure, mucositis may be any kind of mucositis, including oral mucositis (e.g., oral ulceration) or gastrointestinal mucositis. Mucositis may be caused by several reasons. For example, mucositis may occur as an adverse effect of cancer treatment comprising chemotherapy and/or radiotherapy. Several forms of mucosal damage such as those related to herpes simplex virus (HSV) and candida infections can also appear as mucositis.

Conditioning regimen of irradiation and/or chemotherapeutic agents for hematopoietic stem cell transplantation (HSCT) causes mucositis in almost all patients. The monoacetyldiacylglycerol compound may be administered to a patient to prevent or treat mucositis associated with HSCT or peripheral stem cell infusion.

Mucositis may be recurrent oral ulceration. Recurrent oral ulceration can arise as a result of a number of conditions or diseases such as chemotherapy, irradiation therapy, neutropenic conditions and autoimmune diseases. For example, recurrent aphthous stomatitis (RAS), systemic lupus erthematosus (SLE) and Behcet's disease (BD) may cause recurrent oral ulceration. The monoacetyldiacylglycerol compound, especially PLAG, is effective for preventing or treating recurrent oral ulceration caused by these disorders.

The monoacetyldiacylglycerol compound may be administered alone or in combination with an additional agent or therapy treating or alleviating mucositis sequentially or simultaneously. Non-limiting examples of such agents or therapies include, for example, Palifermin (human recombinant keratinocyte growth factor), Amifostine, Gelcair, Zilactin, IL-6 antagonists such as anti-IL-6 antibodies and low-level laser therapy (LLLT).

The pharmaceutical composition of the present invention for preventing or treating mucositis may consist of only or substantially pure monoacetyldiacylglycerols of Formula 1, especially PLAG, or may include active components (monoacetyldiacylglycerols of Formula 1, especially PLAG) and conventional pharmaceutically acceptable carriers, excipients, or diluents. The amount of monoacetyldiacylglycerol in the pharmaceutical composition can be widely varied without specific limitation, and is specifically 0.0001 to 100 weight %, e.g., 0.001 to 50 weight %, 0.01 to 20 weight %, 50-95 weigh % or 95-99 weight % with respect to the total amount of the composition. The pharmaceutical composition may be formulated into solid, liquid, gel or suspension form for oral or non-oral administration, for example, tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as fillers, bulking agents, binders, wetting agents, disintegrating agents, and surfactants can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various excipients such as wetting agents, sweeting agents, flavoring agents, and preserving agents. The formulation for non-oral administration includes sterilized aqueous solution, non-aqueous solution, freeze-dried formulation, suppository, and so on, and solvent for such solution may include propylene glycol, polyethylene glycol, vegetable oils such as olive oil, and ester for syringe injection such as ethyl oleate. Base materials of the suppository may include witepsol, macrogol, tween 61, cacao butter, Laurin and glycerogelatin.

The monoacetyldiacylglycerol compound can be administered in a pharmaceutically effective amount. The term "pharmaceutically effective amount" is used to refer to an amount that is sufficient to achieve a desired result in a medical treatment. The "pharmaceutically effective amount" can be determined according to the subject's category, age, sex, severity and type of disease, activity of drug, sensitivity to drug, administration time, administration route, excretion rate, and so forth.

The term "prevention" or "preventing" includes any activity to suppress or delay onset of mucositis by administering the composition of the present invention. The term "treatment" or "treating" includes prophylaxis, mitigation, amelioration, delay or reduction of symptoms, as well as partial or complete elimination or prevention of symptoms, of mucositis by administering the composition of the present invention. The composition of the present invention can be administered alone or with other medicines sequentially or simultaneously. The preferable amount of the composition of the present invention can be varied according to the condition and weight of patient, severity of disease, formulation type of drug, administration route and period of treatment. An appropriate total amount of administration per 1 day can be determined by a physician, and is generally about 0.05 to 200 mg/kg. Extrapolating from in vivo experiments in animals and in vitro experiments in cells, the preferable total administration amount per day is determined to be 0.1 to 100 mg/kg for an adult human. For example, the total amount of 50 mg/kg can be administered once a day or can be administered in divided doses twice, three, or four times daily.

For example, in one embodiment, the invention provides a pharmaceutical composition for preventing or treating mucositis, in unit dose form, in the form of a soft gelatin capsule for oral administration containing 250-1000 mg, e.g., 250 mg or 500 mg, of PLAG, free of other triglycerides, together with 0.1-3 mg, e.g. 1 mg of a pharmaceutically acceptable tocopherol compound, e.g., α-tocopherol, as an antioxidant, e.g., for administration once or twice a day, at a daily dosage of 500 mg to 4,000 mg, for example 1000 mg/day administered as a divided dose 500 mg in the morning and 500 mg in the evening.

The composition of the present invention can be administered to any subject that requires the prevention or treatment of mucositis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous (i.v.), intramuscular (i.m.), subcutaneous (s.c.) or cerebrovascular injection.

In another embodiment, the present invention provides a health functional food composition for preventing, treating or improving mucositis, which comprises an effective amount of monoacetyldiacylglycerol of formula 1, especially PLAG:

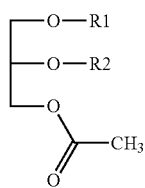

[Formula 1]

wherein $R_1$ and $R_2$ are independently a fatty acid residue of 14 to 20 carbon atoms.

The term "improvement" or "improving" includes any activity to improve symptoms of mucositis by administering the composition of the present invention. The health functional food composition of the present invention for preventing or improving mucositis may consist of only or substantially pure monoacetyldiacylglycerols of Formula 1, especially PLAG, or may include active components (monoacetyldiacylglycerols of Formula 1, especially PLAG) and other conventional ingredients of health functional food. The amount of monoacetyldiacylglycerol in the health food composition can be widely varied and is generally less than 15 weight %, preferably, less than 10 weight %, with respect to the total amount of the health functional food composition. However, the amount of monoacetyldiacylglycerol may be increased or decreased.

Foods to which the compound of the present invention can be added include various foods, for example, meats, sausages, breads, chocolates, candies, snacks, pizzas, noodles, gums, daily products such as ice creams, soups, beverages, teas, drinks, alcoholic beverages, vitamin complexes and animal food.

When the compound of the present invention is used in the beverage product, the beverage product may include sweeting agents, flavoring agents or carbohydrates. Examples of carbohydrates include monosaccharides such as glucose and fructose, disaccharides such as maltose and sucrose, polysaccharides such as dextrin and cyclodextrin, and sugar alcohols such as xylitol, sorbitol and erythritol. The amount of carbohydrate in the beverage composition can be widely varied without specific limitation, and is preferably 0.001 to 0.04 g, more preferably, 0.02 to 0.03 g per 100 ml of the beverage. Examples of sweeting agents include natural sweeteners such as thaumatin and stevia extract and artificial sweeteners such as saccharin and aspartame.

In addition to the above, the health functional food composition of the present invention may include various nutrients, vitamins, electrolytes, flavoring agents, colorants, pectic acid and salts thereof, alginic acid and salts thereof, organic acids, protective colloidal thickening agents, pH controlling agents, stabilizing agents, preserving agents, glycerin, alcohol, carbonizing agents used in carbonated beverages and so on. Moreover, the health functional food composition of the present invention may include fruits, as used in preparing natural fruit juices and fruit juice beverages and vegetable beverages.

The present disclosure thus provides, in one aspect, a method (Method 1) for preventing or treating mucositis, comprising administering to a patient in need thereof an effective amount of a compound of Formula 1:

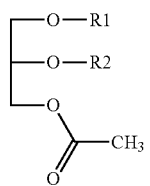

[Formula 1]

wherein $R_1$ and $R_2$ are independently a fatty acid group of 14 to 20 carbon atoms, e.g., PLAG; for example,
1.1. Method 1 wherein $R_1$ and $R_2$ are independently selected from the group consisting of palmitoyl, oleoyl, linoleoyl, linolenoyl, stearoyl, myristoyl, and arachidonoyl.
1.2. Method 1 or 1.1 wherein R1 and R2 (R1/R2) is selected from the group consisting of oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl.
1.3. Any foregoing method wherein the Compound of Formula 1 is a compound of Formula 2:

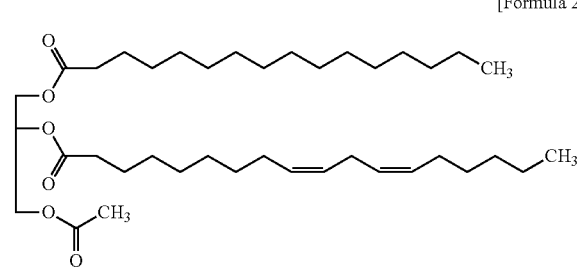

[Formula 2]

1.4. Any foregoing method wherein the compound of Formula 2 is administered in a pharmaceutical composition which is substantially free of other monoacetyldiacylglycerols, e.g., wherein at least 95%, for example at least 99% of the total monoacetyldiacylglycerols in the formulation are of Formula 2.
1.5. Any foregoing method wherein the compound of Formula 2 is administered in a pharmaceutical composition which is substantially free of other monoacetyldiacylglycerol compounds.
1.6. Any foregoing method wherein the compound of Formula 2 is administered in a pharmaceutical composition which is substantially free of other triglyceride compounds.

1.7. Any foregoing method wherein the Compound of Formula 1 is separated and extracted from natural deer antler.
1.8. Any foregoing method wherein the compound of Formula 1 is produced by chemical synthesis.
1.9. Any foregoing method wherein the mucositis is oral mucositis (e.g., oral ulceration) or gastrointestinal mucositis.
1.10. Any foregoing method wherein the mucositis is recurrent oral ulceration.
1.11. Any foregoing method wherein the recurrent oral ulceration is caused by a disease or condition selected from chemotherapy, irradiation therapy, neutropenic condition and autoimmune disease.
1.12. Any foregoing method wherein the recurrent oral ulceration is caused by a disease selected from recurrent aphthous stomatitis (RAS), systemic lupus erthematosus (SLE) and Behcet's disease (BD).
1.13. Any foregoing method wherein the mucositis is caused by an infection such as herpes simplex virus (HSV) and candida infection.
1.14. Any foregoing method wherein the mucositis is caused by cancer therapy comprising chemotherapy and/or radiotherapy.
1.15. Any foregoing method wherein the mucositis is caused in whole or in part by radiation therapy.
1.16. Any foregoing method wherein the mucositis is caused in whole or in part by chemotherapy.
1.17. Any foregoing method wherein the mucositis is caused by a drug selected from Ziv-aflibercept, Brentuximab Vedotin, Deferiprone, Gemcitabine, Pralatrexate, Ganciclovir, Valganciclovir, Thalidomide, Romidepsin, Boceprevir, Decitabine, Imatinib, Topotecan, Lenalidomide, Paclitaxel, Olanzapine, Irinotecan, Paliperidone, Interferons, Lipopolysaccharide, tamoxifen, Flecainide (a class 1C cardiac antiarrhythmic drug), Phenytoin, Indomethacin, Propylthiouracil, Carbimazole, Chlorpromazine, Trimethoprim/sulfamethoxazole (cotrimoxazole), Clozapine, Ticlodipine, and their derivatives, Cyclophosphamide, Mechlorethanime, Chlorambucil, Melphalan, Carmustine(BCNU), Lomustine(CCNU), Procarbazine, Dacarbazine (DTIC), Altretamine, Cisplatin, Carboplatin, Actinomycin D, Etoposide, Topotecan, Irinotecan, Doxorubicin & daunorubicin, 6-Mercaptopurine, 6-Thioguanine, Idarubicin, Epirubicin, Mitoxantrone, Azathioprine, 2-Chloro deoxyadenosine, Hydroxyurea, Methotrexate, 5-Fluorouracil, Cytosine arabinoside, Azacytidine, Fludarabine phosphate, Vincristine, Vinblastine, Vinorelbine, Paclitaxel, Docetaxel, Tamoxifen, Pemetrexed, Nab-paclitaxel, Dasatinib, Paralatrexate, Decitabine, Romidepsin, Imatinib, Lenalidomide, Sunitinib, Oxaliplatin, Adriamycin, Ifosfamide, Cytarabine and Thalidomide.
1.18. Any foregoing method wherein the patient is intending to receive chemotherapy or radiation therapy at a dose sufficient to cause mucositis in the absence of other treatment, or suffering from mucositis consequent to chemotherapy or radiation therapy.
1.19. Any foregoing method wherein the mucositis is associated with hematopoietic stem cell transplantation or peripheral stem cell infusion.
1.20. Any foregoing method wherein the method further comprises administering to a patient in need thereof an effective amount of an additional agent treating or alleviating mucositis sequentially or simultaneously.
1.21. Any foregoing method wherein the additional agent is selected from the group consisting of Palifermin (human recombinant keratinocyte growth factor), Amifostine, Gelcair, Zilactin, IL-6 antagonists (e.g., anti-IL-6 antibodies) and a mixture thereof.
1.22. Any foregoing method wherein the method further comprises an additional therapy treating or alleviating mucositis such as low-level laser therapy (LLLT).
1.23. Any foregoing method wherein the compound of Formula 1, e.g., PLAG, is administered in the form of a pharmaceutical composition for oral administration.
1.24. Any foregoing method wherein the compound of Formula 1, e.g., PLAG, is administered in the form of a pharmaceutical composition which is a soft gelatin capsule containing the Compound of Formula 1, e.g., PLAG, in combination or association with a pharmaceutically acceptable diluent or carrier, for example wherein the pharmaceutically acceptable diluent or carrier comprises an edible oil, e.g., a vegetable oil, for example olive oil.
1.25. Any foregoing method wherein the compound of Formula 1, e.g., PLAG, is administered in the form of a pharmaceutical composition comprising 0.0001 to 100.0 weight %, for example 50-95%, or 95-99%, by weight of the composition.
1.26. Any foregoing method wherein the composition further comprises a pharmaceutically acceptable antioxidant, for example ascorbic acid (AA, E300) and tocopherols (E306), as well as synthetic antioxidants such as propyl gallate (PG, E310), tertiary butylhydroquinone (TBHQ), butylated hydroxyanisole (BHA, E320) and butylated hydroxytoluene (BHT, E321), for example α-tocopherol.
1.27. Any foregoing method wherein the compound of Formula 1, e.g., PLAG, is a compound of Formula 2 administered in the form of a soft gelatin capsule containing 250 mg or 500 mg of the Compound of Formula 1, e.g., PLAG, in combination or association with approximately 50 mg of a pharmaceutically acceptable diluent or carrier, for example an edible oil, e.g., a vegetable oil, e.g., olive oil.
1.28. Any foregoing method wherein the Compound of Formula 1, e.g., PLAG, is administered in the form of a health functional food, for example as an additive or admixture to a food suitable for human consumption.
1.29. Any foregoing method wherein the Compound of Formula 1, e.g., PLAG, is administered once a day (q.d.) or twice a day (b.i.d.).
1.30. Any foregoing method wherein the total daily dosage of the Compound of Formula 1, e.g., PLAG, 250 mg to 2000 mg/day, for example 500 mg-1500 mg/day, e.g., 500 mg/day, 1000 mg/day, or 1500 mg/day.
1.31. Any foregoing method wherein the Compound of Formula 1, e.g., PLAG, is administered in a dosage of 250 mg or 500 mg twice a day, e.g., morning and evening.
1.32. Any foregoing method wherein the Compound of Formula 1, e.g., PLAG, is administered in a dosage of 500 mg once a day, e.g., in the evening.
1.33. Any of the foregoing methods wherein the Compound of Formula 1, e.g., PLAG, is administered over a period of at least two weeks, e.g., at least a month.
1.34. Any foregoing method wherein the pharmaceutical composition may be formulated into solid, liquid, gel or suspension form for oral or non-oral administration.
1.35. Any foregoing method wherein the compound of formula 1, e.g., PLAG, is administered in the form of a soft gelatin capsule for oral administration containing 250-1000 mg of a compound of Formula 1, e.g., PLAG, substantially free of other triglycerides, together with 0.1-3 mg of a pharmaceutically acceptable tocopherol compound.

1.36. Any foregoing method wherein the compound of formula 1, e.g., PLAG, is administered in the form of a soft gelatin capsule for oral administration containing 250 mg or 500 mg of a compound of Formula 1, e.g., PLAG, substantially free of other triglycerides, together with 1 mg of a pharmaceutically acceptable tocopherol compound, administered once or twice a day.

1.37. Any foregoing method wherein the compound of formula 1 is a compound of Formula 2 (PLAG), administered in the form of a soft gelatin capsule for oral administration containing 250 mg or 500 mg of PLAG drug substance and 1 mg α-tocopherol as an antioxidant, administered once or twice a day, at a total daily dosage of 250 mg to 4,000 mg.

1.38. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

1.39. Any foregoing method wherein the treatment is prophylactic.

1.40. Any foregoing method wherein the patient is a human.

1.41. Any foregoing method wherein the patient is an animal.

The present disclosure additionally provides a compound of Formula 1, e.g., PLAG, (or a pharmaceutical composition, e.g., as herein described, comprising an effective amount of a compound of Formula 1, e.g., PLAG) for use in preventing or treating mucositis, e.g., for use in any of Methods 1, et. seq.

The present disclosure additionally provides the use of a compound of Formula 1, e.g., PLAG, in the manufacture of a medicament for preventing or treating mucositis, e.g. in any of Methods 1, et. seq.

The present disclosure additionally provides a health functional food composition comprising an effective amount of a compound of Formula 1, e.g., PLAG, for use in preventing, treating or improving mucositis, e.g., for use in any of Methods 1, et. seq.

The following examples are provided for better understanding of this invention. However, the present invention is not limited by the examples.

EXAMPLE 1

In Vivo Effect of PLAG on Oral Ulceration

Total 44 patients with recurrent oral ulceration (ROU) between 20 and 80 years old (34 female patients and 10 male patients, Disease; RAS (26 patients), BD (27 patients), SLE (1 patient), Mean age: 49.3±9.0) were enrolled in the study. The diagnosis of ROU was made based upon the history and the physical examination on oral mucosa by physicians. We included three conditions with recurrent oral ulceration: Recurrent aphthous stomatitis (RAS), Behcet's disease (BD), Systemic lupus erythematosus (SLE). After completing baseline assessments, 250 mg of PLAG was administered to the patients orally twice a day (250 mg PLAG per tablet, 500 mg/day) for 2-4 weeks. The change of recurrent oral ulcer in the patients was evaluated at 2 or 4 weeks after the treatment by using self-reported scoring system (total 12 points), including the following three measurements: change of ulcer frequency (Likert 0-4), Change of ulcer severity: pain & size (Likert 0-4) and Change of ulcer duration (Likert 0-4). The symptom of ROU was considered to be significantly improved when the sum of the three scores was more than 5 points. The results are shown in table 1.

TABLE 1

| patient | age | sex | period of treatment | condition | change of ulcer frequency | change of ulcer severity | change of ulcer duration | total | significant improvement |
|---|---|---|---|---|---|---|---|---|---|
| 1 | 48 | F | 30 d | BD | 3 | 3 | 4 | 10 | 1 |
| 2 | 62 | F | 30 d |  | 2 | 2 | 2 | 6 | 1 |
| 3 | 54 | F | 30 d |  | 3 | 2 | 3 | 8 | 1 |
| 4 | 58 | F | 30 d |  | 2 | 2 | 3 | 7 | 1 |
| 5 | 53 | F | 30 d | RAS | 2 | 2 | 1 | 5 | 1 |
| 6 | 67 | F | 30 d |  | 2 | 0 | 0 | 2 | 0 |
| 7 | 43 | F | 30 d |  | 2 | 2 | 3 | 7 | 1 |
| 8 | 22 | M | 30 d |  | 2 | 3 | 1 | 6 | 1 |
| 9 | 40 | F | 30 d | RAS | 2 | 2 | 3 | 7 | 1 |
| 10 | 43 | M | 30 d |  | 2 | 3 | 2 | 7 | 1 |
| 11 | 50 | F | 30 d |  | 1 | 2 | 1 | 4 | 0 |
| 12 | 44 | F | 30 d |  | 1 | 2 | 1 | 4 | 0 |
| 13 | 37 | F | 30 d | BD | 3 | 3 | 2 | 8 | 1 |
| 14 | 34 | F | 30 d | BD | 3 | 3 | 2 | 8 | 1 |
| 15 | 58 | F | 30 d | SLE | 1 | 2 | 1 | 4 | 0 |
| 16 | 53 | F | 30 d | BD | 1 | 2 | 1 | 4 | 0 |
| 17 | 57 | F | 30 d | RAS | 3 | 3 | 2 | 8 | 1 |
| 18 | 53 | F | 30 d | RAS | 3 | 2 | 2 | 7 | 1 |
| 19 | 33 | F | 30 d | RAS | 3 | 3 | 3 | 9 | 1 |
| 20 | 30 | F | 30 d | RAS | 1 | 2 | 1 | 4 | 0 |
| 21 | 54 | M | 30 d | BD | 2 | 1 | 2 | 5 | 1 |
| 22 | 49 | F | 14 d | RAS | 3 | 3 | 2 | 8 | 1 |
| 23 | 43 | M | 14 d | BD | 1 | 2 | 2 | 5 | 1 |
| 24 | 44 | F | 30 d | BD | 2 | 1 | 0 | 3 | 0 |
| 25 | 57 | F | 30 d | BD | 2 | 2 | 2 | 6 | 1 |
| 26 | 40 | M | 30 d | RAS | 3 | 3 | 4 | 10 | 1 |

TABLE 1-continued

| patient | age | sex | period of treatment | condition | change of ulcer frequency | change of ulcer severity | change of ulcer duration | total | significant improvement |
|---|---|---|---|---|---|---|---|---|---|
| 27 | 46 | F | 30 d | BD | 1 | 2 | 1 | 4 | 0 |
| 28 | 50 | F | 30 d | RAS | 2 | 3 | 2 | 7 | 1 |
| 29 | 38 | F | 30 d | BD | 2 | 3 | 3 | 8 | 1 |
| 30 | 53 | F | 30 d | RAS | 1 | 1 | 1 | 3 | 0 |
| 31 | 80 | F | 30 d | RAS | 2 | 3 | 2 | 7 | 1 |
| 32 | 71 | F | 30 d | RAS | 2 | 1 | 1 | 4 | 0 |
| 33 | 31 | F | 30 d | BD | 3 | 1 | 1 | 5 | 1 |
| 34 | 56 | F | 30 d | RAS | 2 | 1 | 2 | 5 | 1 |
| 35 | 61 | F | 30 d | RAS | 1 | 1 | 2 | 4 | 0 |
| 36 | 25 | F | 30 d | RAS | 3 | 2 | 2 | 7 | 1 |
| 37 | 64 | F | 14 d | RAS | 2 | 1 | 1 | 4 | 0 |
| 38 | 58 | F | 30 d | BD | 3 | 4 | 4 | 11 | 1 |
| 39 | 49 | F | 30 d | BD | 2 | 2 | 2 | 6 | 1 |
| 40 | 55 | M | 30 d | RAS | 3 | 4 | 2 | 9 | 1 |
| 41 | 52 | M | 30 d | BD | 2 | 3 | 2 | 7 | 1 |
| 42 | 43 | M | 30 d | RAS | 1 | 2 | 1 | 4 | 0 |
| 43 | 54 | M | 30 d | RAS | 2 | 1 | 1 | 4 | 0 |
| 44 | 56 | M | 30 d | RAS | 2 | 2 | 2 | 6 | 1 |
| average | 49.3 | M 10 | | | 2.07 | 2.14 | 1.86 | 5.93 | 30 |
| standard deviation | 9.0 | F 34 | | | 0.55 | 0.68 | 0.72 | 1.76 | 30/44 (68.18%) |

As shown in table 1, change of ulcer frequency (Likert 0-4), change of ulcer severity: pain & size (Likert 0-4) and change of ulcer duration (Likert 0-4) by the administration of PLAG to patients with recurrent oral ulcer are 2.07±0.55, 2.13±0.68 and 1.86±0.72 on average, respectively. The sum of the three scores is 5.93±1.76 on average. 30 out of 44 patients (68.18%) showed significant improvement in recurrent oral ulceration. In the study, any clear side effect of PLAG was not identified. However, one patient showed mild skin rash, two patients showed mild dyspepsia and one patient showed mild taste change (metallic taste). We cannot exclude the possibility that these might be related to the administration of PLAG.

EXAMPLE 2

Unit Dosage Formulation

An exemplary soft gelatin capsule for use in the methods described herein, containing (i) PLAG and (ii) α-tocopherol, is prepared, having a composition as follows:

TABLE 2

Composition of PLAG Softgel Capsules

| Component | Function | Unit Formula |
|---|---|---|
| PLAG | Active Ingredient | 250.0 or 500.0 mg |
| α-tocopherol | Anti-oxidant | 1.0 mg |

TABLE 3

Composition of Soft Capsule Shells

| Ingredients | Function |
|---|---|
| Gelatin | Capsule shell |
| Concentrated glycerin | Plasticizer |
| Methyl para-oxybenzoate | Preservative |
| Propyl para-oxybenzoate | Preservative |
| Ethyl vanillin | Flavor |
| Titanium dioxide | Colorant |
| Tar color, MFDS notified Blue No. 1 | Colorant |
| Tar color, MFDS notified Red No. 40 | Colorant |
| Tar color, MFDS notified Yellow No. 203 | Colorant |
| Purified water | Vehicle |

The invention claimed is:

1. A method for treating mucositis, comprising administering to a patient having mucositis a pharmaceutically effective amount of a compound of Formula 2:

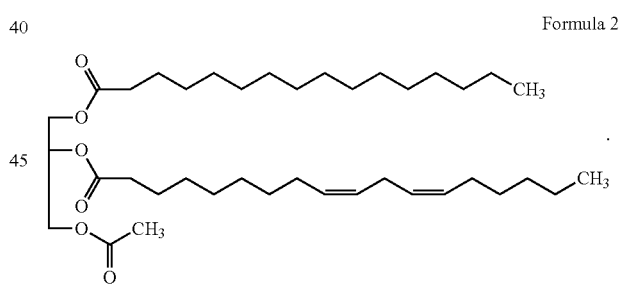

Formula 2

2. The method of claim 1 wherein the compound of Formula 2 is administered in a pharmaceutical composition which is substantially free of other monoacetyldiacylglycerol compounds.

3. The method of claim 1 wherein the compound of Formula 2 is administered in a pharmaceutical composition which is substantially free of other triglyceride compounds.

4. The method of claim 1 wherein the mucositis is oral mucositis or gastrointestinal mucositis.

5. The method of claim 4 wherein the mucositis is oral ulceration.

6. The method of claim 5 wherein the mucositis is recurrent oral ulceration.

7. The method of claim 6 wherein the recurrent oral ulceration is caused by a disease or condition selected from chemotherapy, irradiation therapy, neutropenic condition and autoimmune disease.

8. The method of claim 7 wherein the recurrent oral ulceration is caused by a disease selected from recurrent aphthous stomatitis (RAS), systemic lupus erythematosus (SLE) and Behcet's disease (BD).

9. The method of claim 1 wherein the mucositis is caused by an infection.

10. The method of claim 9 wherein the infection is herpes simplex virus (HSV) or candida infection.

11. The method of claim 1 wherein the mucositis is caused in whole or in part by radiation therapy.

12. The method of claim 1 wherein the mucositis is caused in whole or in part by chemotherapy.

13. The method of claim 12 wherein the mucositis is caused by a drug selected from Ziv-aflibercept, Brentuximab Vedotin, Deferiprone, Gemcitabine, Pralatrexate, Ganciclovir, Valganciclovir, Thalidomide, Romidepsin, Boceprevir, Decitabine, Imatinib, Topotecan, Lenalidomide, Paclitaxel, Olanzapine, Irinotecan, Paliperidone, Interferons, Lipopolysaccharide, Tamoxifen, Flecainide, Phenytoin, Indomethacin, Propylthiouracil, Carbimazole, Chlorpromazine, Trimethoprim/sulfamethoxazole (cotrimoxazole), Clozapine, Ticlodipine, and their derivatives, Cyclophosphamide, Mechlorethanime, Chlorambucil, Melphalan, Caunustine (BCNU), Lomustine(CCNU), Procarbazine, Dacarbazine (DTIC), Altretamine, Cisplatin, Carboplatin, Actinomycin D, Etoposide, Topotecan, Irinotecan, Doxorubicin & daunorubicin, 6-Mercaptopurine, 6-Thioguanine, Idarubicin, Epirubicin, Mitoxantrone, Azathioprine, 2-Chloro deoxyadenosine, Hydroxyurea, Methotrexate, 5-Fluorouracil, Cytosine arabinoside, Azacytidine, Fludarabine phosphate, Vincristine, Vinblastine, Vinorelbine, Paclitaxel, Docetaxel, Tamoxifen, Pemetrexed, Nab-paclitaxel, Dasatinib, Paralatrexate, Decitabine, Romidepsin, Lenalidomide, Sunitinib, Oxaliplatin, Adriamycin, Ifosfamide, Cytarabine and Thalidomide.

14. The method of claim 13 wherein the patient is intending to receive chemotherapy at a dose sufficient to cause mucositis in the absence of other treatment, or suffering from mucositis consequent to chemotherapy.

15. The method of claim 1 wherein the mucositis is associated with hematopoietic stem cell transplantation or peripheral stem cell infusion.

16. The method of claim 1 wherein the method further comprises administering to a patient in need thereof an effective amount of an additional agent sequentially or simultaneously.

17. The method of claim 16 wherein the additional agent is selected from the group consisting of Palifermin, Amifostine, Gelcair, Zilactin, IL-6 antagonists (e.g., anti-IL-6 antibodies) and a mixture thereof.

18. The method of claim 1 wherein the method further comprises low-level laser therapy (LLLT).

19. The method of claim 1 wherein the treatment is prophylactic.

20. The method of claim 1 wherein the compound of Formula 2 is administered in a pharmaceutical composition and the pharmaceutical composition may be formulated into solid, liquid, gel or suspension form for oral or non-oral administration.

21. The method of claim 20 wherein the compound of Formula 2 is administered in the form of a pharmaceutical composition for oral administration.

22. The method of claim 21 wherein the compound of Formula 2 is administered in the form of a pharmaceutical composition which is a soft gelatin capsule containing the compound of Formula 2 in combination or association with a pharmaceutically acceptable diluent or carrier.

23. The method of claim 22 wherein the total daily dosage of the compound of Formula 2 is 250 mg to 2000 mg/day.

24. The method of claim 23 wherein the composition further comprises a pharmaceutically acceptable antioxidant.

25. The method of claim 24 wherein the pharmaceutically acceptable antioxidant is selected from ascorbic acid (AA, E300), tocopherols (E306), propyl gallate (PG, E310), tertiary butylhydroquinone (TBHQ), butylated hydroxyanisole (BHA, E320) and butylated hydroxytoluene (BHT, E321).

26. The method of claim 25 wherein the compound of Formula 2 is administered in the form of a soft gelatin capsule for oral administration containing 250-1000 mg of a compound of Formula 2, substantially free of other triglycerides, together with 0.1-3 mg of a pharmaceutically acceptable tocopherol compound.

27. The method of claim 26 wherein the compound of Formula 2 is administered in the form of a soft gelatin capsule for oral administration containing 250 mg or 500 mg of a compound of Formula 2, substantially free of other triglycerides, together with 1 mg of a pharmaceutically acceptable tocopherol compound, administered once or twice a day.

* * * * *